United States Patent
Arkoff et al.

(10) Patent No.: US 12,380,144 B1
(45) Date of Patent: *Aug. 5, 2025

(54) SYSTEM AND METHOD FOR MEDICAL DATA GOVERNANCE USING LARGE LANGUAGE MODELS

(71) Applicant: OneSource Solutions International, INC, Sudbury, MA (US)

(72) Inventors: Harold Arkoff, Sudbury, MA (US); Vedran Jukic, Trieste (IT)

(73) Assignee: OneSource Solutions International, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/680,985

(22) Filed: May 31, 2024

Related U.S. Application Data

(63) Continuation of application No. 18/417,511, filed on Jan. 19, 2024, now Pat. No. 12,001,464.

(51) Int. Cl.
| | |
|---|---|
| *G06F 16/3332* | (2025.01) |
| *G06F 21/62* | (2013.01) |
| *G06F 40/40* | (2020.01) |
| *G16H 40/20* | (2018.01) |

(52) U.S. Cl.
CPC ...... *G06F 16/3334* (2019.01); *G06F 21/6245* (2013.01); *G06F 40/40* (2020.01); *G16H 40/20* (2018.01)

(58) Field of Classification Search
CPC .. G06F 16/3334; G06F 40/40; G06F 21/6245; G16H 40/20
See application file for complete search history.

(56) References Cited

U.S. PATENT DOCUMENTS

| | | | |
|---|---|---|---|
| 2020/0327964 A1* | 10/2020 | Zhang | G06F 40/295 |
| 2024/0029850 A1* | 1/2024 | Cordell | G16H 50/70 |
| 2024/0029901 A1* | 1/2024 | Ezhov | G16H 10/60 |
| 2024/0078451 A1* | 3/2024 | Neumann | G06N 3/09 |

* cited by examiner

*Primary Examiner* — Fan S Tsang
*Assistant Examiner* — David F Siegel
(74) *Attorney, Agent, or Firm* — IP CONSULTING GROUP; Michael Razavi; Alfred F. Hoyte, Jr.

(57) ABSTRACT

A system for medical data governance using large language models is disclosed. The system receives a user input including at least one search query to retrieve first medical data from one or more medical data governance (MDG) databases. The system applies one or more large language models (LLMs) on the received at least one search query, wherein the one or more LLMs are pre-trained models. The system determines metadata associated with the at least one search query based on the application of the one or more LLMs on the received search query. The system queries a first MDG database of the one or more MDG databases based on the determined metadata to retrieve the first medical data. The system outputs the retrieved first medical data.

20 Claims, 8 Drawing Sheets

SYSTEM AND METHOD FOR MEDICAL DATA GOVERNANCE USING LARGE LANGUAGE MODELS

FIELD OF TECHNOLOGY

The present disclosure relates generally to medical data governance, and more specifically to a system and method for medical data governance using large language models.

BACKGROUND

In recent years, the proliferation of digital health records, coupled with the advancements in artificial intelligence and natural language processing, has created a need for governance of healthcare data. Healthcare systems worldwide are generating vast volumes of sensitive medical data, ranging from patient records and diagnostic imaging to genomic information, presenting both opportunities and challenges in its governance, security, and accessibility. The management and governance of such medical data have become increasingly critical in modern healthcare systems.

Traditional approaches to medical data governance often face challenges in maintaining data integrity, protecting patient confidentiality, complying with regulatory requirements, and transmitting data sharing effectively in facilitating empowered agencies. The sheer complexity and sensitivity of medical information present unique challenges that require innovative solutions for improved governance. The need for robust processes to ensure data integrity, confidentiality, and compliance with regulatory frameworks has never been greater.

Furthermore, the evolution of medical data management has been marked by challenges in accessing and querying disparate databases (or repositories) while ensuring strict compliance with regulatory frameworks governing sensitive healthcare information. Traditional systems often necessitate rigid query formats and specific languages, impeding seamless access to comprehensive medical data. Therefore, there is also a requirement for a system that can process user queries in their preferred language (say English, Spanish, and the like) and also in a conversational style as compared to formatted queries that may be difficult for some users to understand and write, thereby restricting them from using the available medical data.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY OF THE DISCLOSURE

Systems and/or methods are provided for medical data governance using large language models, substantially as shown in and/or described in connection with at least one of the figures, as set forth more completely in the claims.

In contemporary healthcare ecosystems, the management and utilization of medical data have emerged as pivotal components in delivering quality patient care, advancing medical research, and enhancing healthcare outcomes. The exponential growth of healthcare data, however, has introduced complexities and challenges, particularly concerning the governance, privacy, security, and ethical handling of sensitive medical information.

Medical data, characterized by its diversity, sensitivity, and voluminous nature, spans across multiple sources, including electronic health records (EHRs), medical imaging, genomic data, wearable devices, and more. This wealth of data presents a treasure trove of insights that can significantly augment medical diagnoses, treatment planning, and healthcare innovations. However, the effective utilization of this data is impeded by multifaceted challenges.

One of the foremost challenges pertains to the intricate regulatory landscape governing healthcare data. Regulations and various other global frameworks necessitate stringent adherence to standards ensuring the privacy, security, and ethical use of medical data. Compliance with these regulations demands sophisticated systems that can navigate complex data governance requirements while enabling seamless data access and utilization.

Moreover, the fragmentation of medical data across disparate systems and institutions amplifies the challenge of interoperability and data integration. The heterogeneity in data formats, structures, and systems across healthcare facilities hampers the efficient exchange and aggregation of information critical for comprehensive individual patient care, research endeavors, healthcare analytics, and large population datasets.

By amalgamating mature cutting-edge technologies (such as Large Language models) and robust governance frameworks, the disclosed system endeavors to transcend the barriers hindering efficient data utilization in healthcare. Its envisioned impact extends beyond facilitating data access, promising to elevate healthcare outcomes, foster groundbreaking research endeavors, and uphold the highest standards of data ethics and governance in the ever-evolving landscape of modern medicine.

Also, the disclosers represent a paradigm shift in the realm of healthcare informatics, addressing these hurdles through a system designed to process natural language queries effortlessly across multiple databases (or repositories) without imposing constraints on format or language. This innovation harnesses the power of advanced natural language processing (NLP) technologies and Large Language Models (LLMs), enabling users to articulate inquiries in their preferred language and conversational style.

Specifically, the disclosure bridges linguistic barriers and database disparities, facilitating the extraction of pertinent medical information scattered across diverse data databases. Its unique capability lies in its adherence to stringent medical data governance protocols, ensuring compliance with regulatory frameworks governing the privacy, security, and ethical use of healthcare data.

By amalgamating cutting-edge LLM and NLP algorithms with robust data governance mechanisms, this disclosure unlocks a new dimension in healthcare data accessibility. It empowers healthcare professionals, researchers, and stakeholders to interact with complex medical data ecosystems seamlessly. This approach not only streamlines information retrieval but also fosters a comprehensive understanding of patient health profiles and enables evidence-based decision-making in clinical settings and medical research endeavours.

Therefore, the disclosed innovative fusion of linguistic flexibility, database interoperability, and regulatory compliance sets a new benchmark in the fusion of technology and healthcare, promising transformative advancements in patient care, both individual and large populations, research, and healthcare analytics.

Certain embodiments of the disclosure may be found in a system, a method, a computer readable medium, and/or an apparatus for medical data governance using large language models. Various embodiments of the disclosure may provide the system that may include circuitry configured to receive a user input including at least one search query to retrieve first medical data from one or more medical data governance databases. The system may further apply one or more large language models (LLMs) on the received at least one search query. The one or more LLMs may be pre-trained models. The system may further determine metadata associated with the at least one search query based on the application of the one or more LLMs on the received search query. The system may further query a first medical data governance database of the one or more medical data governance databases based on the determined metadata to retrieve the first medical data. The system may further output the retrieved first medical data.

Nowadays, regulatory bodies, such as those from Europe, are creating boundaries to artificial intelligence (AI) for ethical purposes. For example, Artificial Intelligence (AI) is prohibited to be trained on personal identifiable data. This disclosure as embodied here, is to use medical data governance to configure general LLMs to provide meaningful data about a specific patient, without recording and training any LLM model about a specific patient, so the data and AI may not be misused.

The disclosed system transposes structured data (numerical, textual and trends) into written language construction that LLM may use to profile, learn and generate meaningful answers to queries. The disclosed system creates results using metadata from an LLM Query, from the first medical data governance database. This structured data, associated with the determined metadata, is expressed as a configuration to LLM in the form of specific language terms and sentences used to train the LLM (English or German, for example). The LLM query creates a specific syntax for medical data governance, based on the context of the question and previous queries.

In accordance with an embodiment, the system may extract, from the first medical data governance database, raw structured data associated with the determined metadata based on querying the first medical data governance database. The system then, based on query metadata and raw data received, constructs multiple LLM configurations that may be specific to metadata and raw data. The system may further retrieve the first medical data based on the constructed LLM configurations. The system may further output the retrieved first medical data.

In accordance with an embodiment, the medical data governance database comprises of electronic medical records associated with at least one user.

In accordance with an embodiment, the electronic medical records correspond to at least one of: doctor consultation notes, doctor progress notes, nurses notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with at least one user.

In accordance with an embodiment, the system may acquire numerical data captured by one or more medical devices associated with at least one user. The system may further generate a description associated with the received numerical data. The system may further store the generated description in at least one of the one or more medical data governance databases.

In accordance with an embodiment, the system may receive real-time medical data associated with at least one user from one or more medical devices associated with the at least one user. The system may further determine at least one upcoming event associated with a medical condition of the at least one user based on the received real-time medical data and the one or more medical data governance databases. The system may further output the determined at least one upcoming event.

In accordance with an embodiment, the system may determine at least one keyword from the determined metadata. The at least one keyword is associated with the at least one search query. The system may further select the first medical data governance database of the one or more medical data governance databases based on the determined at least one keyword. The system may further query the selected first medical data governance database of the one or more medical data governance databases.

In accordance with an embodiment, the at least one keyword corresponds to one of a name of a user, a name of a medical facility, a name of a disease, or a name of a medical procedure.

DETAILED DESCRIPTION OF THE DISCLOSURE

Figure 1:
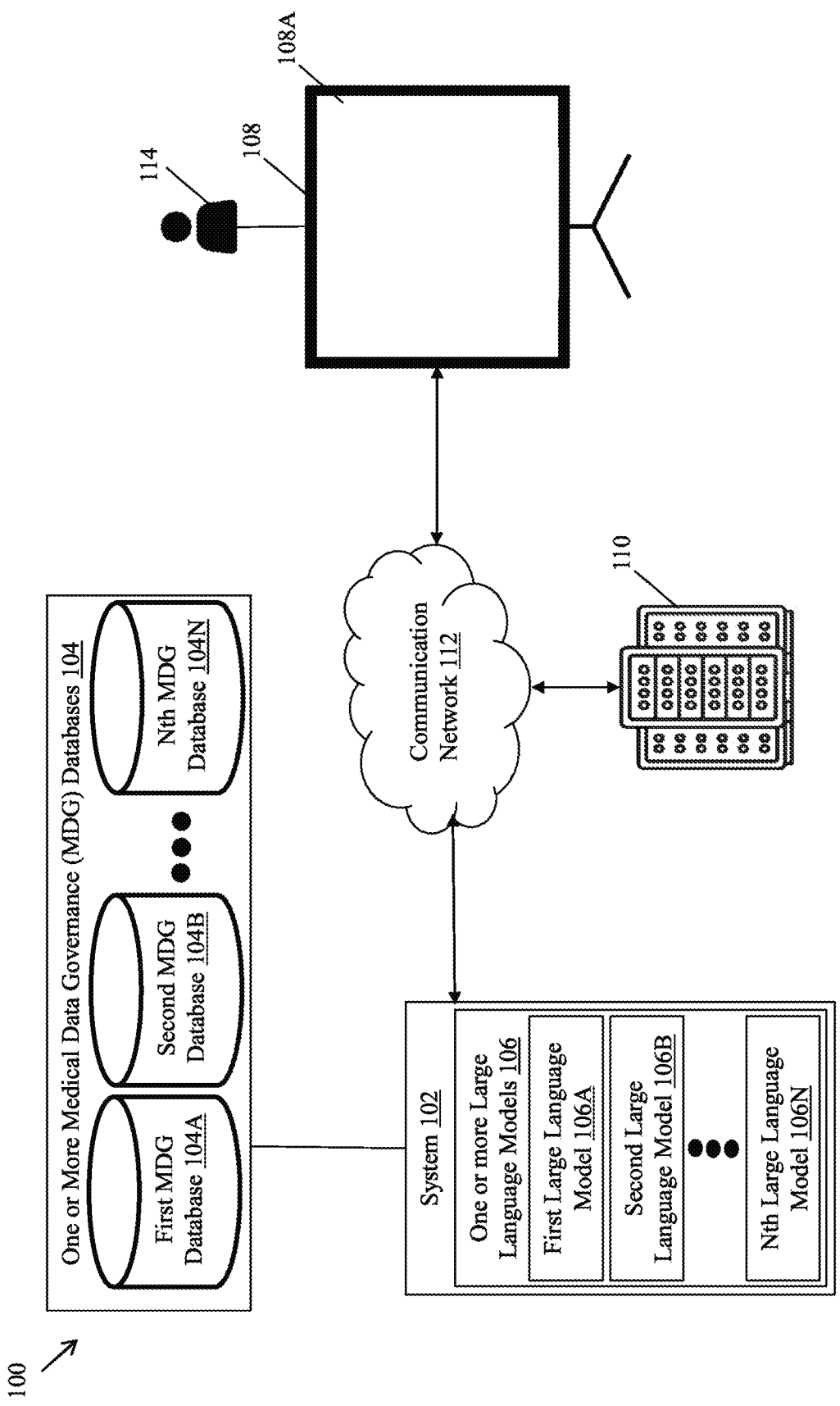
FIG. 1 is a block diagram that illustrates an exemplary environment for medical data governance using large language models, in accordance with an exemplary embodiment of the disclosure.

Various aspects of the disclosure may be found in a method and system for medical data governance using large language models. With the digitization in the medical field, the management and governance of medical data have become increasingly critical in modern healthcare systems. Specifically, with the digitization of patient records, advancements in medical technology, and the ever-growing volume of healthcare data, ensuring the security, integrity, and responsible use of this information has emerged as a pivotal concern. Traditional methods of medical data management often encounter challenges in maintaining data accuracy, protecting patient privacy, adhering to regulatory requirements, and facilitating efficient data sharing among authorized entities. The complexity and sensitivity of medical data pose unique challenges that necessitate innovative solutions for robust governance.

The principal impediment to the advancement and adoption of artificial intelligence (AI) within critical care environments is the absence of a robust infrastructure and research tools for data capable of gathering high-frequency, unfiltered, and time-synchronized data directly from all available medical devices associated with patients, and before they get filtered, reduced and stripped from metadata and stored in the clinical patient record.

In the realm of medical imaging, the proliferation of unfiltered imaging data accompanied by diagnostic information and patient outcomes has fostered the development of numerous AI applications founded on machine learning algorithms.

Simply put, the main reason AI isn't used more widely in critical care is because of the lack of infrastructure to collect and process the data necessary for training and using AI systems. This data needs to be collected in real-time, without any unnecessary transformations, from all the medical devices that patients use. Additionally, it may be of utmost importance that this data is organized and normalized in a way that AI systems can understand and use effectively.

The medical imaging field is a good example of how AI can be used to improve patient care. The AI models may be been trained on large datasets of unfiltered medical images to identify diseases and predict patient outcomes. However, to achieve similar results in critical care environments, there is a requirement to develop a better way to collect and process data from medical devices.

In recent years, with the advent of advanced technologies artificial intelligence (AI)-based solutions, in particular, have demonstrated their potential in transforming the landscape of medical data governance. Specifically, large language models (LLMs), powered by deep learning algorithms, have emerged as transformative tools capable of understanding, processing, and generating human-like text at an unprecedented scale and depth. In the healthcare sector, the application of the LLMs presents a compelling opportunity to revolutionize medical data governance. By harnessing the power of these LLMs, there exists the potential to address key challenges in data quality enhancement, privacy preservation, regulatory compliance, and semantic understanding and insights.

Medical Data Governance may be important for several reasons, including protecting the privacy of patients, ensuring the quality of data, and promoting the ethical use of data. For example, medical data governance helps to protect the privacy of patients by ensuring that their data is collected, stored, and used responsibly. This includes de-identifying data before it is shared with researchers or other third parties. Also, medical data governance helps to ensure the quality of data by ensuring that it is collected, stored, and transmitted consistently and accurately. This helps to reduce the risk of errors and bias in research findings. Furthermore, medical data governance helps to promote the ethical use of data by ensuring that it is used for legitimate purposes and that it is not shared with unauthorized parties. This helps to protect the public trust and to ensure that research is conducted responsibly.

The disclosure proposes a system and method that harnesses the capabilities of LLMs to revolutionize medical data governance. By integrating these LLMs into the fabric of healthcare data management, the innovation outlined herein aims to establish a robust framework for ensuring data accuracy, privacy, regulatory compliance, and enhanced insights extraction while navigating the complexities inherent in managing vast volumes of sensitive medical information.

FIG. 1 is a block diagram that illustrates an exemplary environment for medical data governance using large language models, in accordance with an exemplary embodiment of the disclosure. Referring to FIG. 1, there is shown a network environment 100, which may include a system 102, one or more medical data governance (MDG) databases 104, one or more (LLMs) 106, a user device 108 that includes a display device 108A, a server 110, and a communication network 112. The one or more MDG databases 104 may include a first MDG database 104A, a second MDG database 104B, up to an Nth MDG database 104N. Similarly, the one or more LLMs 106 may include a first LLM 106A, a second LLM 106B, a third LLM 106C, up to an Nth LLM 106N. With reference to FIG. 1, there is further shown a user 114 associated with the user device 108.

The system 102 may comprise suitable logic, circuitry, interfaces, and/or code that may be configured to receive a user input including at least one search query to retrieve first medical data from the one or more MDG databases 104. The first medical data corresponds to the information that may be requested by the user. In some embodiments, the system 102 may be further configured to apply the one or more LLMs 106 on the received at least one search query. The system 102 may be further configured to determine metadata associated with the at least one search query based on the application of the one or more LLMs 106 on the received search query. The system 102 may be further configured to query at least the first MDG database 104A of the one or more MDG databases 104 based on the determined metadata to retrieve the first medical data. The system 102 may be further configured to output the retrieved first medical data. Examples of the system 102 may include, but are not limited to, a computing device, a mainframe machine, a server, a computer workstation, a smartphone, a cellular phone, a mobile phone, a gaming device, and/or a consumer electronic (CE) device with image processing capabilities.

In an embodiment, the system 102 may correspond to a MDG (MDG) system that may enable medical data governance (MDG). As discussed above, MDG provides a true source of data that can highlight the schedule of medical treatments and provides tools for rescheduling feedback, contacting and receiving feedback from patients/physicians/healthcare professionals thus introducing general system flexibility through the use of lean process and six sigma methods. MDG leverages modern communication methods (phone apps, emails, web services, etc.) and easily links patient's physicians, or other healthcare professionals to the scheduled use of medical devices. After unexpected events that may cause a miss in scheduled operations, the MDG may create a backup schedule to pre-emptively fill the gaps and may facilitate healthcare and schedule professionals to optimize machine time usage. This could create a new marketplace for priority services for those patients who opt for it.

Also, MDG may enable patients/users and or institutions to monetize their vital, medically relevant, patient data collected during the stay inside the healthcare institution, as well through the extended data collected over some time in multiple stays or spot measurements in healthcare institutions. Patients may be able to establish a relationship with a third party (such as a drug manufacturer, independent drug trial projects, undisclosed trials to the institution) and provide to the third party normalized data collected, organized, and provided by the MDG used by the healthcare institution, and provided to the patient in a different standardized format, even in near real-time. The institution might not be aware of the final user of the patient data. MDG can create additional revenue for the institution by charging such a service per patient and data processed. MDG can track and trace data usage per patient and assets. MDG through the export of all specific, validated clinical data, and medical relevant data, could create a new data-based economy.

Furthermore, MDG manages patient consent and approval, or notification for the use of the patient data for second opinions, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.). MDG can handle patient consent using modern communication methods (phone apps, emails, web services, etc.) and provide patient consent for his data to be used in a specific research or validation project, with or without compensation. MDG can provide patient consent and access to the data to specific users, like doctors, physicians, and other specific medical professionals. MDG can provide specific code associated with the data, that, based on necessity, can provide, if granted by the user or proxy consent, protected personal identification, family relations, or other protected personal data MDG may allow for third-party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable datasets.

Each of the one or more MDG databases 104 may correspond to a structured collection of organized information stored electronically in a way that enables easy access, retrieval, and manipulation of medical data. The one or more MDG databases 104 may serve as a centralized database where the medical data may be systematically arranged into tables, records, and fields, following a predefined data model. The one or more MDG databases 104 may be designed to efficiently manage vast amounts of information, allowing users to perform queries, insert new data, update existing records, and delete information based on specific requirements. In an embodiment, the one or more MDG databases 104 may correspond to a storage system associated with the MDG. Examples of different types of the one or more MDG databases 104 may include, but are not limited to, a relational database, a non-relational database, a document database, and a graph database.

Each of the one or more LLMs 106 may correspond to a sophisticated artificial intelligence (AI) system trained on vast amounts of text data, capable of understanding, generating, and processing human-like language at an extensive scale. Each of the one or more LLMs 106 models utilizes deep learning techniques, particularly transformer architectures, enabling them to grasp context, syntax, semantics, and even nuances in language usage. The primary function of the one or more LLMs 106 may involve, but is not limited to, natural language processing tasks like text generation, translation, summarization, and sentiment analysis. Each of the one or more LLMs 106 may learn to predict and generate text by analysing patterns and relationships within the massive corpus of text they've been trained on. Examples of different types of the one or more LLMs 106 may include, but are not limited to, a Transformer-Based Model, a Bidirectional Encoder Representations from Transformers (BERT) model, a Generative Pre-trained Transformer (GPT) model, a Unified Language Model, and a Text-to-Text Transfer Transformer (T5) model.

In an embodiment, each of the one or more LLMs 106 may include a neural network that may be a computational network or a system of artificial neurons, arranged in a plurality of layers, as nodes. The plurality of layers of each of the neural network may include an input layer, one or more hidden layers, and an output layer. Each layer of the plurality of layers may include one or more nodes (or artificial neurons). Outputs of all nodes in the input layer may be coupled to at least one node of hidden layer(s). Similarly, inputs of each hidden layer may be coupled to outputs of at least one node in other layers of the corresponding neural network. Outputs of each hidden layer may be coupled to inputs of at least one node in other layers of the corresponding neural network. Node(s) in the final layer may receive inputs from at least one hidden layer to output a result. The number of layers and the number of nodes in each layer may be determined from hyper-parameters of the corresponding neural network model. Such hyper-parameters may be set before or while training the corresponding neural network model on a training dataset.

The neural network may correspond to a mathematical function (for example, a sigmoid function or a rectified linear unit) with a set of parameters, tuneable during training of the network. The set of parameters may include, for example, a weight parameter, a regularization parameter, and the like. Each node may use the mathematical function to compute an output based on one or more inputs from nodes in other layer(s) (for example, previous layer(s)) of the corresponding neural network model. All or some of the nodes of the each of the set of neural network models may correspond to the same or different mathematical function.

In training of the neural network, one or more parameters of each node of the corresponding neural network may be updated based on whether an output of the final layer for a given input (from the training dataset) matches a correct result based on a loss function for the corresponding neural network. The above process may be repeated for the same or a different input until a minima of loss function may be achieved, and a training error may be minimized. Several methods for training are known in art, for example, gradient descent, stochastic gradient descent, batch gradient descent, gradient boost, meta-heuristics, and the like.

Each of the set of neural network may include electronic data, such as a software program, code of the software program, libraries, applications, scripts, or other logic or instructions for execution by a processing device, such as hardware processor. Each of the set of neural network models may include code and routines configured to enable a computing device, such as the system 102, to perform one or more operations. Additionally or alternatively, the neural network may be implemented using hardware including a processor, a microprocessor, a field-programmable gate array (FPGA), or an application-specific integrated circuit (ASIC) to perform or control performance of one or more operations. Alternatively, in some embodiments, each of the neural network model may be implemented using a combination of hardware and software.

Although in FIG. 1, the one or more LLMs 106 are shown as integrated within the system 102, the disclosure is not so limited. Accordingly, in some embodiments, the one or more LLMs 106 may be associated with the system 102, without deviation from the scope of the disclosure. In an embodiment, the one or more LLMs 106 may be stored in the server 110.

The user device 108 may include suitable logic, circuitry, interfaces, and/or code that may be configured to receive one or more user inputs (for example at least one search query) from the user 114 and transmit the received one or more user inputs to the system 102. The system 102 may be further configured to display the first medical data on the display device 108A associated with the user device 108. Examples of the user device 108 may include, but are not limited to, a computing device, a computer work-station, a smartphone, a cellular phone, a mobile phone, a gaming device, a consumer electronic (CE) device, a mainframe machine, or a server.

The display device 108A may comprise suitable logic, circuitry, and interfaces that may be configured to display the first medical data. In accordance with an embodiment, the display device 108A may be a touch screen which may enable the user to provide the one or more user inputs via the display device 108A. The touch screen may be at least one of a resistive touch screen, a capacitive touch screen, or a thermal touch screen. The display device 108A may be realized through several known technologies. Examples of such technologies may include, but are not limited to, at least one of a Liquid Crystal Display (LCD) display, a Light Emitting Diode (LED) display, a plasma display, or an Organic LED (OLED) display technology, or other display devices.

The server 110 may include suitable logic, circuitry, and interfaces, and/or code that may be configured to store the at least one search query. The server 110 may be further configured to store the one or more MDG databases 104 and the one or more LLMs 106. In some embodiments, the server 110 may be configured to train each of the one or more LLMs 106. The server 110 may be implemented as a cloud server and may execute operations through web applications, cloud applications, HTTP requests, database operations, file transfer, and the like. Other example implementations of the server 110 may include, but are not limited to, a database server, a file server, a web server, a media server, an application server, a mainframe server, or a cloud computing server.

In at least one embodiment, the server 110 may be implemented as a plurality of distributed cloud-based resources by use of several technologies that are well known to those ordinarily skilled in the art. A person with ordinary skill in the art will understand that the scope of the disclosure may not be limited to the implementation of the server 110 and the system 102 as two separate entities. In certain embodiments, the functionalities of the server 110 can be incorporated in its entirety or at least partially in the system 102, without a departure from the scope of the disclosure.

The communication network 112 may include a communication medium through which the system 102, the one or more MDG databases 104, the one or more LLMs 106, the user device 108, the display device 108A, and the server 110 may communicate with each other. The communication network 112 may be one of a wired connection or a wireless connection. Examples of the communication network 112 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 112 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

In operation, the system 102 may be configured to receive the user input including at least one search query to retrieve first medical data from one or more MDG databases 104. In an embodiment, the at least one search query is written in a first language. The first language may correspond to any natural language (say English). In an embodiment, the natural language may refer to a way humans may communicate using spoken or written words in everyday conversation(s). The natural language may have its grammar, vocabulary, syntax, and rules for constructing meaningful expressions, allowing individuals to convey complex ideas and emotions. Examples of the natural languages include English, Spanish, Mandarin, and the like.

The system 102 may be further configured to apply the one or more LLMs 106 on the received at least one search query. As discussed above, the one or more LLMs 106 may be pre-trained models. In an embodiment, the one or more LLMs 106 may get iteratively trained based on new user requests. The system 102 may be further configured to determine metadata associated with the at least one search query based on the application of the one or more LLMs on the received search query. Based on the determined metadata, the system 102 may be further configured to query the first MDG database 104A of the one or more MDG databases 106. The first MDG database 104A may be queried to retrieve the first medical data. The system 102 may be further configured to output the retrieved first medical data. The output of the retrieved first medical data may correspond to the rendering of the first medical data on the display device 108A associated with the user device 108.

Figure 2:
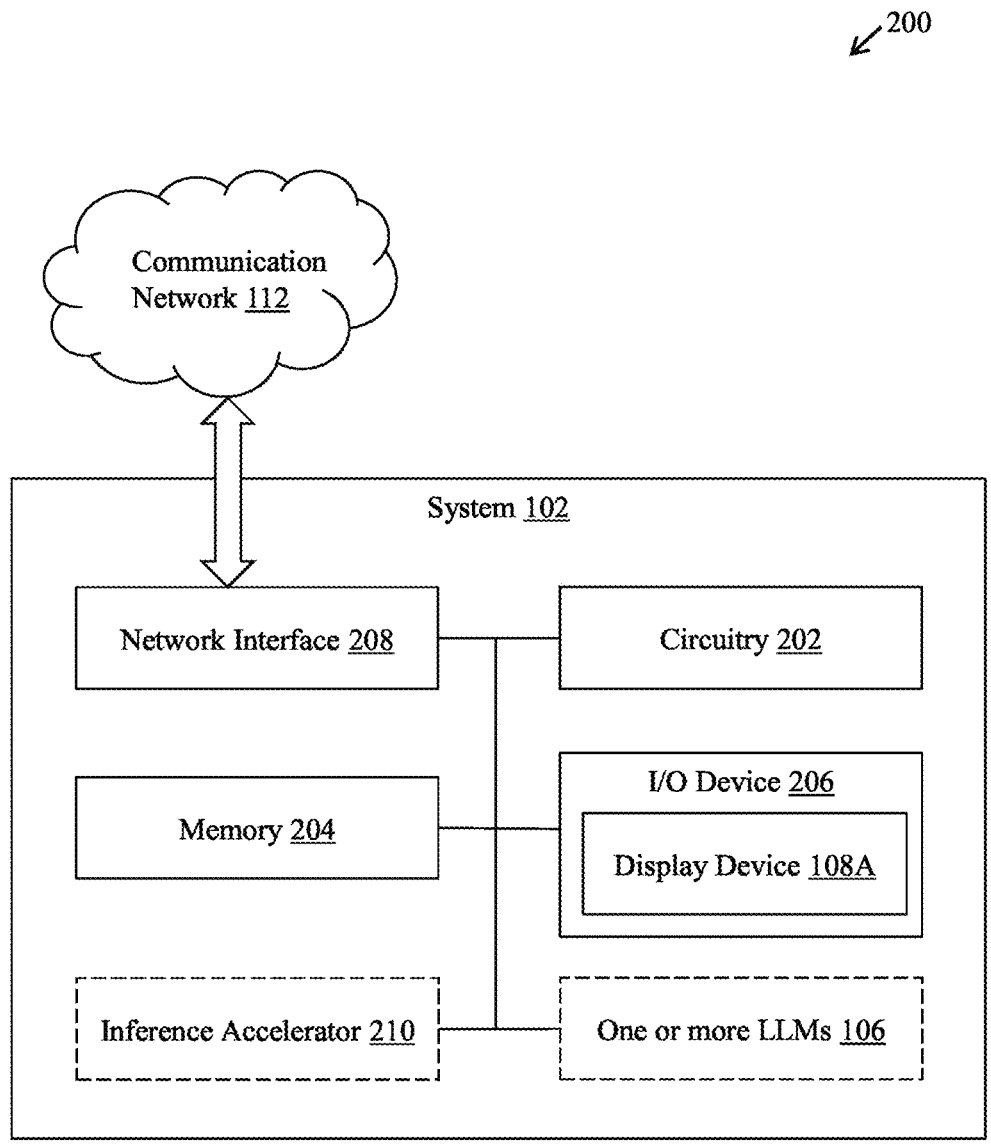
FIG. 2 is a block diagram that illustrates an exemplary system for medical data governance using large language models, in accordance with an embodiment of the disclosure.

FIG. 2 is a block diagram that illustrates an exemplary system for medical data governance using large language models, in accordance with an embodiment of the disclosure. FIG. 2 is explained in conjunction with elements from FIG. 1. With reference to FIG. 2, there is shown a block diagram 200 of the system 102. The system 102 may include a circuitry 202, a memory 204, an input/output (I/O) device 206, a network interface 208, an inference accelerator 210, and the one or more LLMs 106. The circuitry 202 may be communicatively coupled to the memory 204, the I/O device 206, the network interface 208, the inference accelerator 210, and the one or more LLMs 106.

The circuitry 202 may include suitable logic, circuitry, and interfaces that may be configured to execute program instructions associated with different operations to be executed by the system 102. For example, some of the operations may include, but are not limited to, receiving the user input, applying the one or more LLMs 106, determining metadata, querying the first MDG database 104A, and outputting the retrieved first medical data. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other computing circuits.

The memory 204 may include suitable logic, circuitry, interfaces, and/or code that may be configured to store the program instructions to be executed by the circuitry 202. In at least one embodiment, the memory 204 may store the at least one search query. The memory 204 may also store the one or more LLMs 106. In an embodiment, the memory 204 may be further configured to store first medical data, raw data, and the one or more MDG databases 104. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and interfaces that may be configured to receive one or more user inputs and provide an output. For example, the system 102 may receive the user input via the I/O device 206. The I/O device 206 may further display the retrieved first medical data. The I/O device 206 which includes various input and output devices, may be configured to communicate with the circuitry 202. Examples of the I/O device 206 may include, but are not limited to, a touch screen, a keyboard, a mouse, a joystick, a microphone, a display device, and a speaker.

The network interface 208 may include suitable logic, circuitry, and interfaces that may be configured to facilitate a communication between the circuitry 202, the one or more MDG databases 104, the one or more LLMs 106, the user device 108, the display device 108A, and the server 110, via the communication network 112. The network interface 208 may be implemented by use of various known technologies to support wired or wireless communication of the system 102 with the communication network 112. The network interface 208 may include, for example, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet, or a wireless network, such as a cellular telephone network, a public switched telephonic network (PSTN), a radio access network (RAN), a wireless local area network (LAN), and a metropolitan area network (MAN). The wireless communication may use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VOIP), light fidelity (Li-Fi), Worldwide Interoperability for Microwave Access (Wi-MAX), a protocol for email, instant messaging, and a Short Message Service (SMS).

The inference accelerator 210 may include suitable logic, circuitry, interfaces, and/or code that may be configured to operate as a co-processor for the circuitry 202 to accelerate computations associated with the operations of the each of the one or more LLMs 106. The inference accelerator 210 may implement various acceleration techniques, such as parallelization of some or all of the operations of the corresponding one or more LLMs 106. The inference accelerator 210 may be implemented as a software, a hardware, or a combination thereof. Example implementations of the inference accelerator 210 may include, but are not limited to, a GPU, a Tensor Processing Unit (TPU), a neuromorphic chip, a Vision Processing Unit (VPU), a field-programmable gate arrays (FGPA), a Reduced Instruction Set Computing (RISC) processor, an Application-Specific Integrated Circuit (ASIC) processor, a Complex Instruction Set Computing (CISC) processor, a microcontroller, and/or a combination thereof.

The functions or operations executed by the system 102, as described in FIG. 2, may be performed by the circuitry 202. Various operations executed by the circuitry 202 are described in detail, for example, in FIGS. 3A, 3B, 4, and 5.

Figure 3:
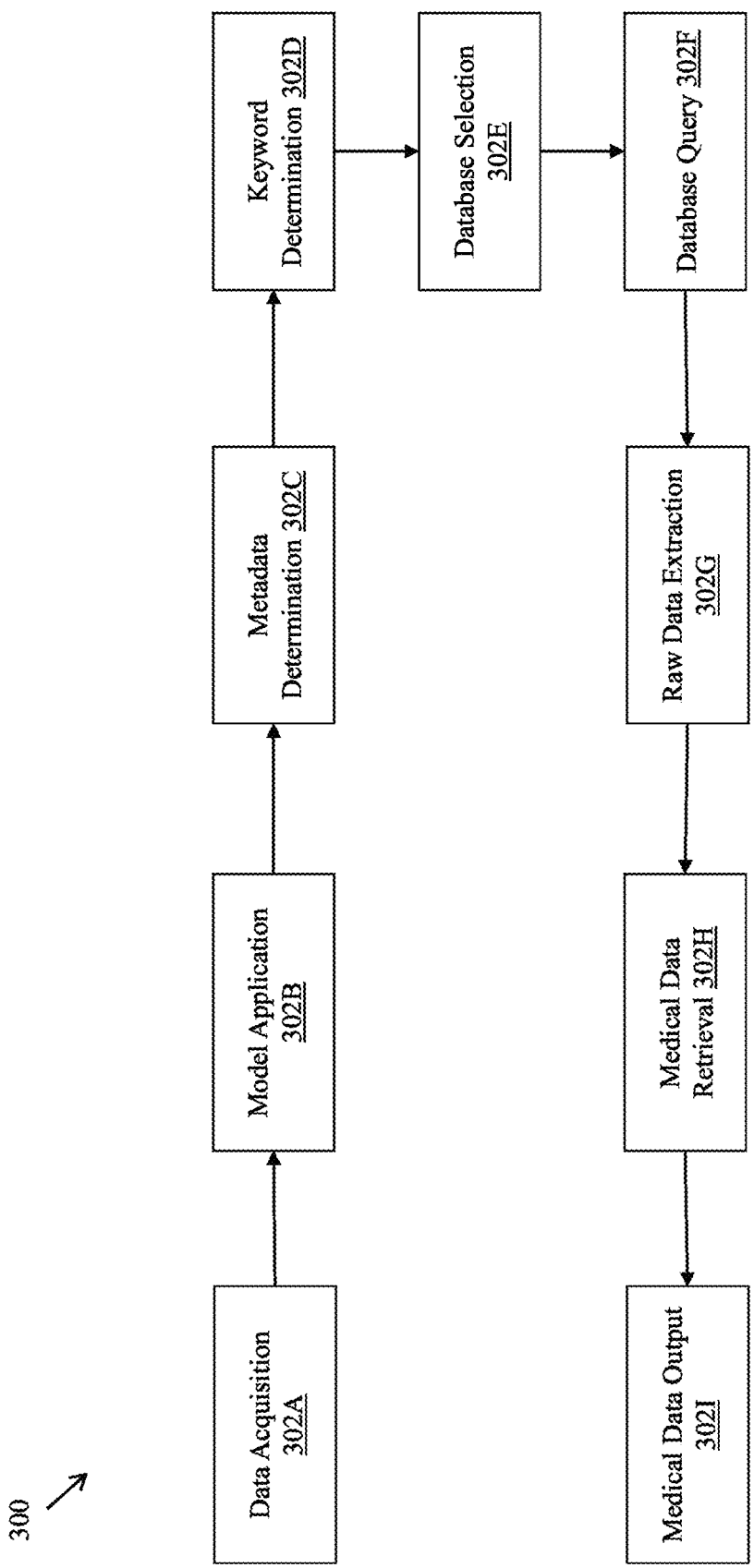
FIG. 3 is a diagram that illustrates exemplary operations for medical data governance using large language models, in accordance with an embodiment of the disclosure.

FIG. 3 is a diagram that illustrates exemplary operations for medical data governance using large language models, in accordance with an embodiment of the disclosure. FIG. 3 is explained in conjunction with elements from FIG. 1 and FIG. 2. With reference to FIG. 3, there is shown a block diagram 300 that illustrates exemplary operations from 302A to 302I, as described herein. The exemplary operations illustrated in the block diagram 300 may start at 302A and may be performed by any computing system, apparatus, or device, such as by the system 102 of FIG. 1 or circuitry 202 of FIG. 2. Although illustrated with discrete blocks, the exemplary operations associated with one or more blocks of the block diagram 300 may be divided into additional blocks, combined into fewer blocks, or eliminated, depending on the particular implementation.

At 302A, a data acquisition operation may be performed. In data acquisition operation, the circuitry 202 may be configured to receive the user input from the user 114 of the system 102. The user 114 may be, for example, a doctor, a physician, or any medical professional in a medical environment. In an embodiment, the user 114 may be a patient or any person from the general public. In an embodiment, the input may be received from the user device 108 via the communication network 112 and may include at least one search query that may be written in a first language (say English). As a first example, the at least one search query may be "Find me a patient that most probably has Sepsis."

In an embodiment, the at least one search query may be received to retrieve the first medical data from the one or more MDG databases 104. Each MDG database of the one or more MDG databases 104 may include electronic medical records associated with at least one user. The electronic medical records (EMRs) may correspond to digital versions of the paper charts in a healthcare provider's office. Such EMRs may include a patient's medical history, diagnoses, medications, treatment plans, immunization dates, allergies, radiology images, laboratory test results, and the like. In an embodiment, the EMRs may allow for systematic storage, retrieval, and modification of patient data, making it easily accessible to authorized healthcare providers. In an embodiment, the one or more MDG databases 104 may correspond to a specific storage and retrieval tool that can work very efficiently with the one or more LLMs 106 to create an interface and a communication tool for doctors to synthesize responses based on context and clarity.

In an embodiment, the EMRs may include medical history reports, physical examination reports, diagnostic reports, progress notes, consultation reports, operative reports, discharge summaries, medication reports, billing reports, and insurance reports. Examples of the EMRs may correspond to at least one of doctor consultation notes, doctor progress notes, nurses notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with at least one user.

In another embodiment, the one or more MDG databases 104 may further include records associated with multiple patients, medical facilities, and medical procedures. The medical facilities encompass diverse settings designed to provide healthcare services and support to individuals. The medical facilities may include, but are not limited to, hospitals, clinics, urgent care centers, rehabilitation centers, and nursing homes. The medical procedures may encompass a vast range of interventions performed by healthcare professionals to diagnose, treat, or prevent various health conditions. Such medical procedures may include diagnostic procedures (such as X-rays, CT scans, MRI scans, ultrasounds, and PET scans), surgical procedures (such as laparoscopy, and arthroscopy), therapeutic procedures (such as chemotherapy, and radiation therapy), cardiovascular procedures (such as angioplasty, coronary artery bypass grafting (CABG)), obstetric and gynecological procedures (such as cesarean section, colposcopy), orthopedic procedures (such as joint replacement, fracture repair), and dental procedures (such as fillings and root canals, and extractions).

At 302B, a model application operation may be executed. In the model application operation, the circuitry 202 may be configured to apply the one or more LLMs 106 on the received at least one search query. As discussed above, each of the one or more LLMs 106 may be pre-trained models that may be trained to extract metadata based on the received at least one search query. In an embodiment, the one or more LLMs 106 may be been trained on all medical textbooks that may be known in the art. As an example, the one or more LLMs 106 may put together about 65 billion words and may be used to provide all metadata needed for successful research and then provide it back as an interface to humans. Specifically, the one or more LLMs 106 may be used as an interface for the research.

At 302C, a metadata determination operation may be executed. In the metadata determination operation, the circuitry 202 may be configured to determine metadata associated with the at least one search query. In an embodiment, the metadata may be determined based on the application of the one or more LLMs 106 on the received search query. The metadata may correspond to information about the data, such as the type of data, the date it was collected, and the patient it is associated with. By indexing the metadata, users (such as doctors) may be able to search for data across MDG databases without having to access the data itself.

In an embodiment, the metadata may be required for successful research. Specifically, the one or more LLMs 106 may be used to provide all metadata that are needed for successful research and provide it back as an interface to the user 114. With reference to the first example, the one or more LLMs 106 by itself may find the metadata needed to define sepsis.

At 302D, a keyword determination operation may be executed. In the keyword determination operation, the circuitry 202 may be configured to determine at least one keyword from the determined metadata. In an embodiment, the least one keyword is associated with the at least one search query. In an embodiment, the at least one keyword corresponds to one of a name of a user, a name of a medical facility, a name of a disease, or a name of a medical procedure.

In an embodiment, the system 102 may be configured to apply the one or more LLMs on the determined metadata to further determine the at least one keyword. In another embodiment, the system 102 may be configured to apply a natural language processing (NLP) model on the metadata to determine the at least one keyword. With reference to the first example, the at least one keyword may be "Sepsis".

At 302E, a database selection operation may be executed. In the database selection operation, the circuitry 202 may be configured to select the first MDG database 104A of the one or more MDG databases 104 based on the determined at least one keyword. In an embodiment, each of the one or more MDG databases 104 may be associated with at least one keyword. For example, the first MDG database 104A may include all the information about the patients associated with at least one medical disease (such as sepsis), the second MDG database 104B may include medical records associated with the set of patients in a geographic area (such as a city or a town), the third MDG database 104C may include details about all the patients, medical equipment, facilities available in at least one medical clinic in the geographic area, and so on.

At 302F, a database query operation may be executed. In the database query operation, the circuitry 202 may be configured to query the selected first MDG database 104A of the one or more MDG databases 104. In an embodiment, querying the first medical database 104A may refer to a process of requesting specific information or data from the first medical database 104A. The system 102 may be configured to query at least the first MDG database 104A of the one or more MDG databases 104 to retrieve the first medical data associated with the at least one search query.

At 302G, a raw data extraction operation may be executed. In the raw data retrieval operation, the circuitry 202 may be configured to extract, from the first MDG database 104A, raw data associated with the determined metadata based on the querying the first MDG database 104A. The raw data may include all the data extracted from the first MDG database 104A that may be associated with the determined at least one keyword. With reference to the first example, the raw data may include a knowledge base associated with the medical disease sepsis, details associated with one or more patients suffering from sepsis in the geographical area, medical facilities offering treatment for sepsis, trends in the people suffering from sepsis, and the like.

At 302H, a medical data retrieval operation may be performed. In the medical data retrieval operation, the circuitry 202 may be configured to retrieve the first medical data. In an embodiment, the system 102 may be configured to retrieve the first medical data from the extracted raw data. To determine the first medical data, the system 102 may be configured to generate one or more constructs associated with the one or more LLMs to be applied on the extracted raw data. The one or more constructs may be associated with the determined metadata. The system 102 may be further configured to retrieve the first medical data based on the application of the generated one or more constructs on the extracted raw data. The first medical data may correspond to an appropriate answer to the at least one search query and may be a desired answer to the at least one search query.

With reference to the first example, the first medical data may correspond to details associated with one or more patients suffering from sepsis in the geographical area. The details may include a name, an age, a sex, an address, a medical history, and the like associated with the one or more patients suffering from the medical disease sepsis.

At 302I, a medical data output operation may be performed. In the medical data output operation, the circuitry 202 may be configured to output the retrieved first medical data. In an embodiment, the output of the retrieved first medical data may correspond to displaying the first medical data on the user device 114. In another embodiment, the output of the first medical data may correspond to storing the first medical data in the one or more MDG databases 104.

In an embodiment, the disclosed system may be configured to create thousands of descriptions (permutations of data elements) results using metadata from an LLM Query, from the first medical data governance database. This structured data, associated with the determined metadata, may be expressed as a configuration to LLM in the form of specific language terms and sentences used to train the LLM (English or German, for example). The LLM query may further create a specific syntax for medical data governance, based on the context of the question and previous queries.

In accordance with an embodiment, the system may extract, from the first medical data governance database, raw structured data associated with the determined metadata based on querying the first medical data governance database. The system then, based on the query metadata and the raw data, constructs one or more LLM configurations that may be specific to metadata and raw data to be further apply the one or more LLMs. The system may further retrieve the first medical data based on the application of the one or more LLMs on the extracted raw data. The system may further output the retrieved first medical data.

In another embodiment, the system 102 (or the MDG system) may enable federated search of medical data. The federated search may allow users to search for data across multiple distributed systems without having to centralize the data in one location. This may be important for protecting the privacy of patients and for reducing the administrative burden on hospitals.

There may be several different approaches to the federated search of medical data. One important approach of MDG is to generate metadata to index the sensitive data. As discussed above, the metadata is information about the data, such as the type of data, the date it was collected, and the patient it is associated with. By indexing the metadata, the users may be able to search for data across multiple systems without having to access the data itself.

Another advantage of the MDG may be that it acts as a centralized storage system for different healthcare systems or medical facilities (such as hospitals) that may be accessed using a query mediator. The query mediator (or the one or more LLMs) may be a component that may acts as an intermediary between the user and the distributed MDG subsystems. The query mediator component receives the user's search query and forwards it to the relevant MDG subsystems, providing unifying results back to the user.

Some specific examples of how federated search of medical data is used may include a researcher may search for data on patients with a particular disease across multiple hospitals. This could help the researcher to identify new risk factors for the disease or to develop new treatments. Another example may be that a clinician may search for data on patients who have had a particular surgery across multiple hospitals. This could help the clinician to learn from the experiences of other surgeons and to improve their surgical outcomes. Another example may be that a patient may use a search for data on their medical history across multiple hospitals. This could help the patient to better understand their health and to make informed decisions about their care.

Therefore, MDG federated search of medical data may be a powerful tool that may be used to improve patient care and to advance medical research. MDG may be essential for enabling federated search in a secure and privacy-preserving manner.

In addition to these general benefits, MDG can also provide a number of specific benefits for research, such as facilitating data sharing, supporting the development of new research methods, and promoting the translation of research findings into clinical practice. Specifically, MDG may facilitate data sharing between researchers, which can help to accelerate research and improve the quality and impact of research findings. MDG may also support the development of new research methods, such as the use of machine learning and artificial intelligence to analyze large datasets. Furthermore, MDG may also help to promote the translation of research findings into clinical practice by ensuring that data is collected and stored in a way that is compatible with clinical systems.

The specific value of MDG for research on patient medical data is that it may allow researchers to access and use large datasets of patient data without compromising the privacy of individual patients. This is possible because MDG may ensure that data is de-identified before it is used for research. Such de-identified patient medical data may be used to conduct a wide range of research studies, including clinical trials, Observational studies, and Basic science research.

Therefore, MDG may be essential for ensuring that medical data is used responsibly and ethically for research. This is important for protecting the privacy of patients, ensuring the quality of data, promoting the ethical use of data, and accelerating the development of new medical treatments and cures.

Figure 4:
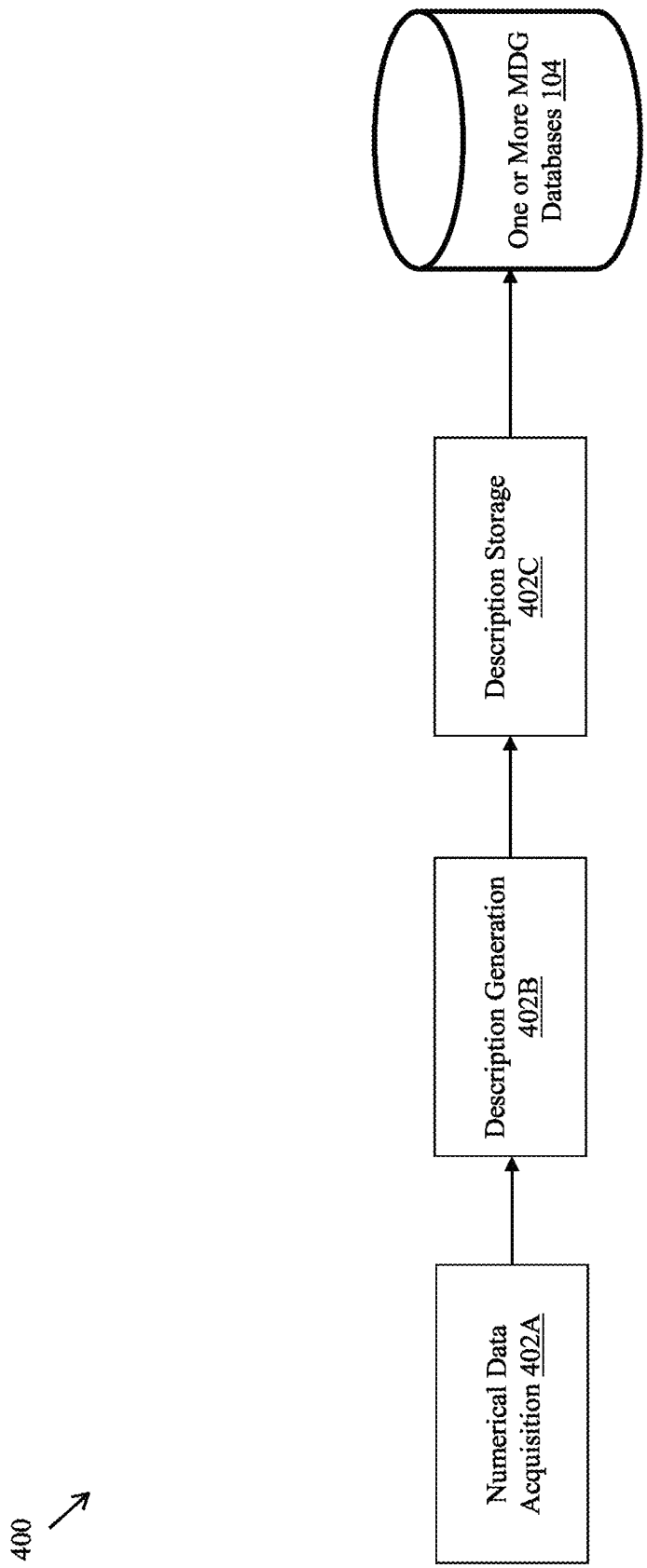
FIG. 4 is a diagram that illustrates exemplary operations for the generation of description associated with numerical data, in accordance with an embodiment of the disclosure.

FIG. 4 is a diagram that illustrates exemplary operations for the generation of description associated with numerical data, in accordance with an embodiment of the disclosure. FIG. 4 is explained in conjunction with elements from FIG. 1, FIG. 2, and FIG. 3. With reference to FIG. 4, there is shown a block diagram 400 that illustrates exemplary operations from 402A to 402C, as described herein. The exemplary operations illustrated in the block diagram 400 may start at 402A and may be performed by any computing system, apparatus, or device, such as by the system 102 of FIG. 1 or circuitry 202 of FIG. 2. Although illustrated with discrete blocks, the exemplary operations associated with one or more blocks of the block diagram 400 may be divided into additional blocks, combined into fewer blocks, or eliminated, depending on the particular implementation.

At 402A, a numerical data acquisition operation may be performed. In the numerical data acquisition operation, the system 102 may be configured to acquire numerical data. The numerical data may refer to information that may be quantifiable and expressed in numerical form. In an embodiment, the numerical data may be captured by one or more medical devices that may be associated with the at least one user. Each of the one or more medical devices may correspond to instruments, tools, machines, implants, software, or any similar item used for medical purposes, including diagnosis, treatment, monitoring, or prevention of diseases or other health conditions. Examples of the one or more medical devices may include a blood glucose meter, a blood pressure meter, an electrocardiogram (ECG) Monitor, a pulse oximeter, and the like. As a second example, the acquired numerical data may be of "Blood Pressure: 82 bpm" or "Blood Oxygen: 98%".

At 402B, a description generation operation may be performed. In the description generation operation, the system 102 may be configured to generate a description associated with the received numerical data. The description may be written in the first language and may involve summarizing and presenting the essential characteristics, patterns, and properties of the acquired numerical data. In an embodiment, the system 102 may be configured to generate descriptions of all numerical data including time segments, variability, range, distribution, and statistical calculations used in medical papers, publications, and medical documentation related to specific patient conditions.

In an embodiment, the system 102 may be configured to apply the NLP model to the acquired numerical data. Based on the application of the NLP model, the system 102 may be configured to generate the description of the acquired numerical data. With reference to the second example, the generated description of the numerical data "Blood Pressure: 82 bpm" may be "The blood pressure of the user may be eighty-two beats per minute".

At 402C, a description storage operation may be performed. In the description storage operation, the system 102 may be configured to store the generated description in at least one of the one or more MDG databases 104. The stored description may be used for medical data retrieval as discussed in the FIG. 3.

Figure 5:
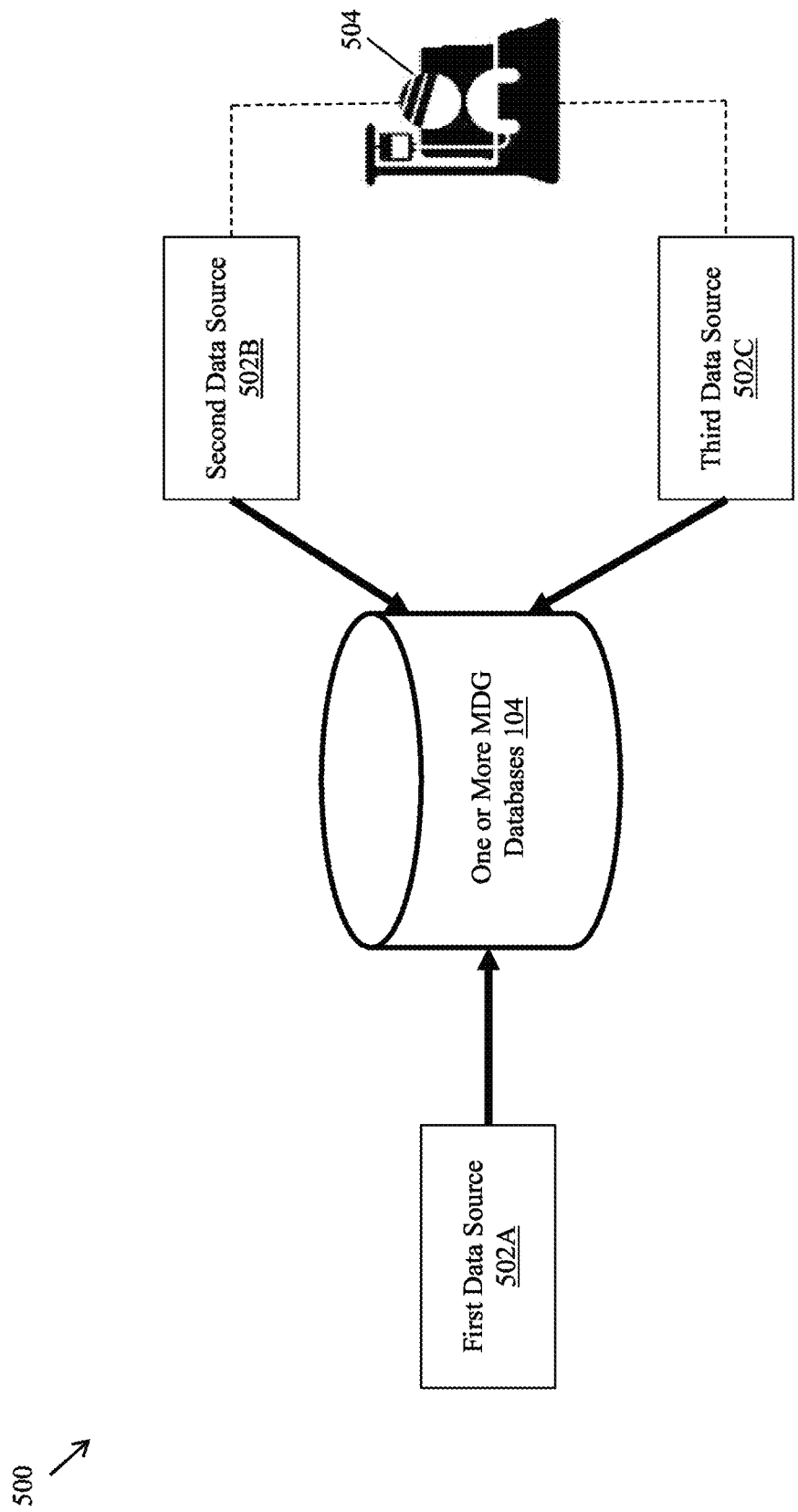
FIG. 5 is a diagram that illustrates a set of data sources for obtaining medical data to be stored in one or more medical data governance databases, in accordance with an embodiment of the disclosure.

FIG. 5 is a diagram that illustrates a set of data sources for obtaining medical data to be stored in one or more medical data governance databases, in accordance with an embodiment of the disclosure. FIG. 5 is explained in conjunction with elements from FIGS. 1, 2, 3, and 4. With reference to FIG. 5, there is shown a diagram 500 that includes a set of data sources 502 for obtaining medical data to be stored in the one or more MDG databases 104. In an embodiment, the set of data sources 502 may include, but is not limited to, a first data source 502A, a second data source 502B, and a third data source 502C.

In an embodiment, the first data source 502A may correspond to legacy medical knowledge. Specifically, the legacy medical knowledge refers to traditional or historical medical practices, theories, and information that have been passed down through generations and may encompass the methods, beliefs, and treatments used in medicine. In an embodiment, the legacy medical knowledge may include textbooks associated with the medical field, research papers associated with the medical field, patents associated with the medical field, publications associated with the medical field, clinical trials, and research databases, healthcare guidelines, and protocols, medical conferences and symposia, drug databases and formularies, public health reports and epidemiological data, and the like.

In an embodiment, the second data source 502B and the third data source 502C may be associated with at least one patient 504 (of multiple patients). The second data source 502B may correspond to medical data that may be obtained from the one or more medical devices (or equipment) that may be associated with the patient 504 to capture corresponding parameters associated with the patient 504. For example, a smart watch associated with (or worn by) the patient 504 may capture the heart rate of the patient 504 and may further store the captured heart rate of the patient 504 in the one or more MDG databases 104.

In some embodiments, the data obtained from the one or more medical devices may include numerical data. In such instances, the system 102 may be configured to obtain the numerical data captured by one or more medical devices associated with the patient 504. The system 102 may be configured to generate a description associated with the received numerical data and further store the generated description in at least one of the one or more MDG databases 104. Details about the generation of the description are provided, for example, in FIG. 4.

In an embodiment, the third data source 502C may be associated with a patient 504 (of multiple patients) and may correspond to medical data that may be obtained from medical records of the patient 504. Such records may include, but are not limited to, doctor consultation notes, doctor progress notes, nurses notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with the patient 504.

In an embodiment, the data generated or stored in the one or more MDG databases 104 may be utilized by the system 102 to train the one or more LLMs 106 to increase the performance of the one or more LLMs 106

Figure 6:
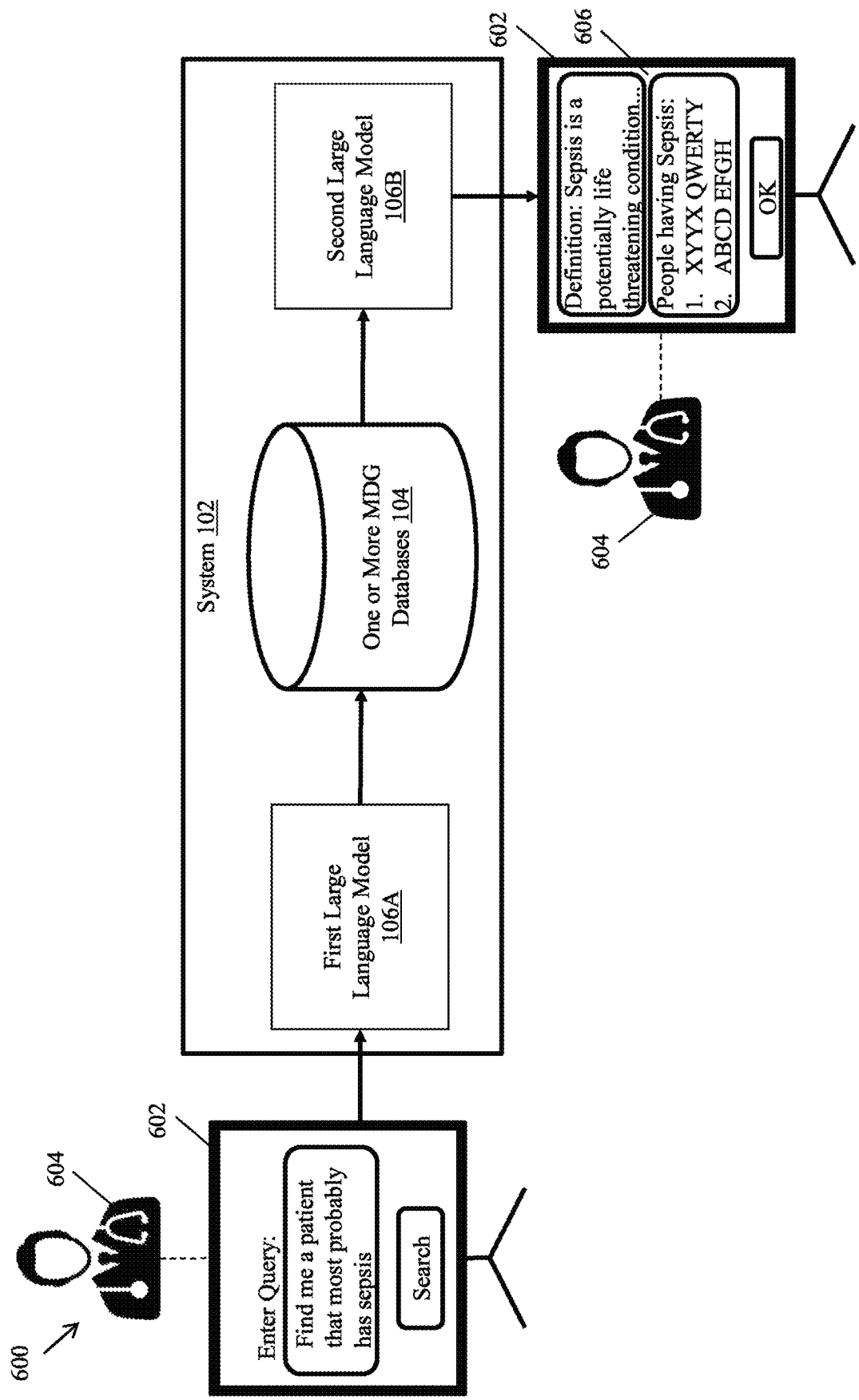
FIG. 6 is a diagram that illustrates an exemplary scenario for an application for medical data governance using large language models, in accordance with an embodiment of the disclosure.

FIG. 6 is a diagram that illustrates an exemplary scenario for an application for medical data governance using large language models, in accordance with an embodiment of the disclosure. FIG. 6 is explained in conjunction with elements from FIGS. 1, 2, 3, 4, and 5. With reference to FIG. 6, there is shown an exemplary scenario 600. There is further shown an electronic device 602 associated with a user 604 who may be a medical professional (for example, a doctor (physician), a nurse, a surgeon, a pharmacist, a dentist, a therapist, and the like).

In an embodiment, the user 604 may wish to determine information related to medical field or related to a patient (say the patient 504) whom the user 604 may be treating. The user 604 may enter a query related to medical field or related to a patient (say the patient 504) whom the user 604 may be treating on the electronic device 602. Based on the reception of the query, the electronic device 602 may transmit the query to the system 102 via the communication network 112. By way of a first example and not limitation, the query may be "Find me a patient that most probably has sepsis".

Based on the reception of the query from the electronic device 602, the system 102 may be configured to apply the one or more large language models (LLMs) 106 on the received at least one search query. Based on the application of the one or more LLMs 106, the system 102 may determine metadata associated with the at least one search query. The one or more LLMs may be pre-trained to determine metadata associated with the search query. With reference to the first example, the one or more LLMs may find what is the metadata needed to define sepsis.

The system 102 may be further configured to query the first MDG 104A of the one or more MDG databases 104 based on the determined metadata to retrieve medical data. The medical data may be associated with the search query and may include at least one person who most probably has sepsis.

In an embodiment, the system 102 may be configured to extract raw data associated with the determined metadata from the first MDG database 104A. System 102 may be further configured to apply the one or more LLMs 106 on the extracted raw data. Specifically, the system 102 may be configured to apply the second LLM 106B of the one or more LLMs 106 on the extracted raw data. Based on the application of the one or more LLMs 106 on the extracted raw data, the system 102 may be configured to retrieve the first medical data. The retrieved first medical data may correspond to an answer to the query "Find me a patient that most probably has sepsis" and may include details about at least one patient who might have sepsis. The system 102 may be further configured to transmit the retrieved first medical data to the electronic device 602. The electronic device 602 may receive the first medical data and render the first medical data on a user interface (UI) of the user device 606.

In another embodiment, the user 604 may use the system 102 to query information related to the patient 504. For example, the user 604 may use the system 102 to determine whether the patient 504 may have a particular medical condition (say sepsis). In such an embodiment, the system 102 may query the one or more MDG databases 104 that may include information associated with a medical history of the patient. The system 102 may further apply the one or more LLMs on the medical history of the patient and generate a response indicating whether the patient may have a particular medical condition (say sepsis).

In another embodiment, the system 102 may be configured to receive real-time medical data associated with at least one user from one or more medical devices associated with (say worn by) the patient 504. Based on the received real-time medical data and the one or more MDG databases, the system 102 may be configured to determine at least one upcoming event associated with a medical condition of the patient 504. The system 102 may be further configured to output the determined at least one upcoming event on the electronic device 602. In another embodiment, the system 102 may trigger audible or visual notifications indicating the at least one upcoming event. By way of example and not limitation, the system 102 may transmit notifications to user devices (or electronic device 602) (such as smartphones or computer(s)) associated with the user 604 or the patient 504.

By way of example and not limitation, the system 102 may receive real-time data associated with the blood pressure of the patient 504 from a smartwatch worn by the patient 504. The received real-time data may indicate an increase in the blood pressure of the patient 504 over a short time period. Based on the received real-time data, and the one or more MDG databases 104 that may include information from legacy medical knowledge, such an increase in blood pressure in a certain time period may be indicative of an upcoming blood pressure attack (or hypertensive crisis). The system 102 may output the determined upcoming blood pressure attack (or hypertensive crisis) on the user device 104. Based on the output of the upcoming blood pressure attack, the user 604 may provide medications to the patient 504 to overcome (or at least to reduce the impact of) the upcoming blood pressure attack. Therefore, the disclosed system 102 may save the lives of the patients automatically without any human intervention.

Figure 7:
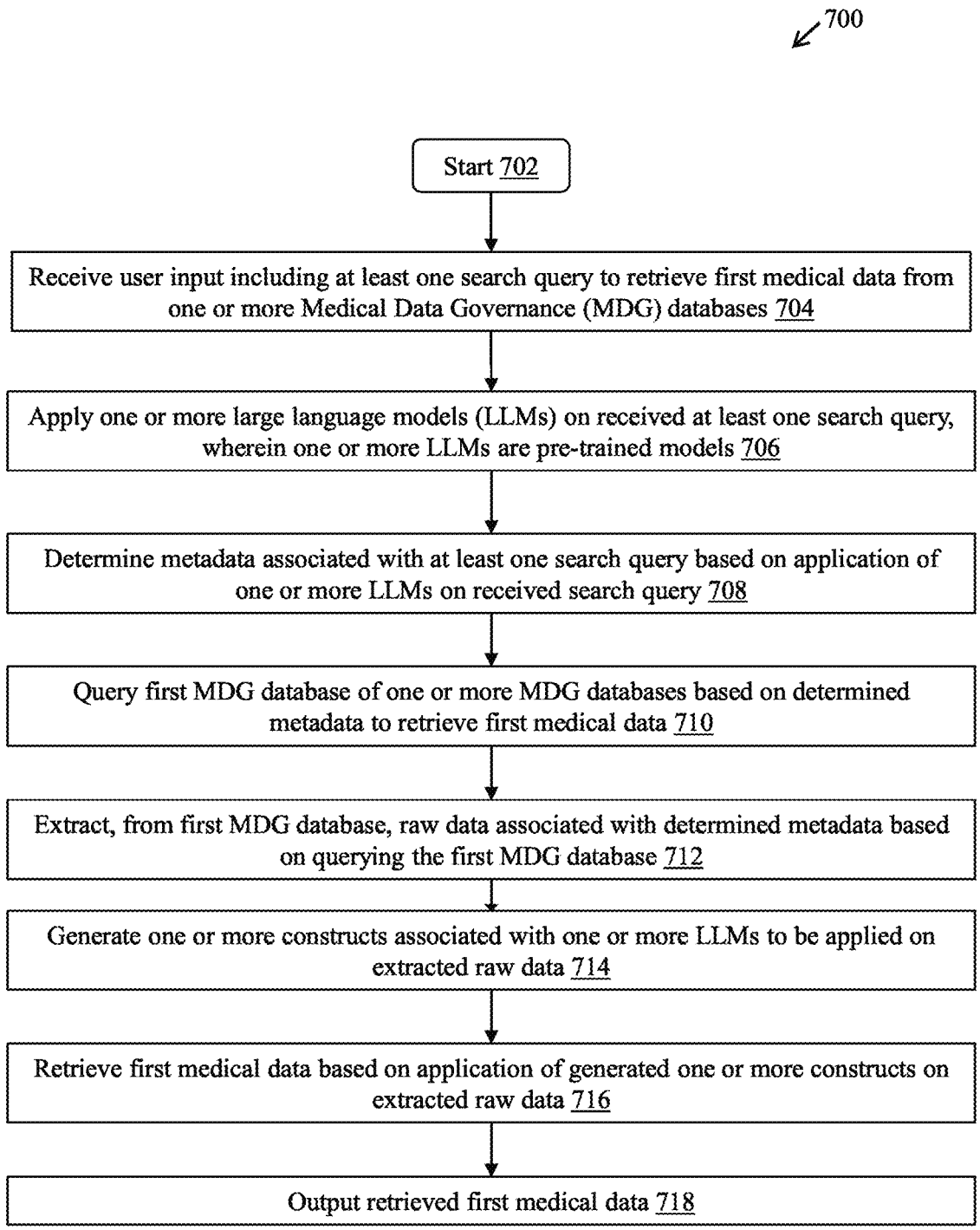
FIG. 7 is a flowchart that illustrates an exemplary method for medical data governance using large language models, in accordance with an embodiment of the disclosure.

FIG. 7 is a flowchart that illustrates an exemplary method for medical data governance using large language models, in accordance with an embodiment of the disclosure. FIG. 7 is explained in conjunction with elements from FIGS. 1, 2, 3, 4, 5, and 6. With reference to FIG. 7, there is shown a flowchart 700. The operations of the exemplary method may be executed by any computing system, for example, by the system 102 of FIG. 1 or the circuitry 202 of FIG. 2. The operations of the flowchart 700 may start at 702 and may proceed to 704.

At 704, the user input may be received. The user input may include at least one search query to retrieve the first medical data from the one or more MDG databases 104. In at least one embodiment, the circuitry 202 may receive the user input including at least one search query to retrieve the first medical data from the one or more MDG databases 104.

At 706, the one or more LLMs 106 may be applied on the received at least one search query. The one or more LLMs 106 may be pre-trained models. In at least one embodiment, the circuitry 202 may apply the one or more LLMs 106 on the received at least one search query, wherein the one or more LLMs 106 may be pre-trained models.

At 708, metadata associated with the at least one search query may be determined. The metadata may be determined based on the application of the one or more LLMs 106 on the received search query. In at least one embodiment, the circuitry 202 may determine metadata associated with the at least one search query based on the application of the one or more LLMs 106 on the received search query.

At 710, the first MDG database 104A of the one or more MDG databases 104 may be queried based on the determined metadata to retrieve the first medical data. In at least one embodiment, the circuitry 202 may query a first MDG database of the one or more MDG databases based on the determined metadata to retrieve the first medical data.

At 712, the raw data associated with the determined metadata may be extracted from the first MDG database based on querying the first MDG database. In at least one embodiment, the circuitry 202 may extract, from the first MDG database, the raw data associated with the determined metadata based on querying the first MDG database.

At 714, the one or more constructs associated with the one or more LLMs may be generated and applied on the extracted raw data. The one or more constructs may be associated with the metadata. In an embodiment, the circuitry 202 may be configured to generate the one or more constructs associated with the one or more LLMs to be applied on the extracted raw data, wherein the one or more constructs are associated with the metadata.

At 716, the first medical data may be retrieved based on application of generated one or more constructs on extracted raw data. In an embodiment, the circuitry 202 may be configured to retrieve the first medical data based on application of generated one or more constructs on extracted raw data.

At 718, the retrieved first medical data may be outputted. In at least one embodiment, the circuitry 202 may output the retrieved first medical data. Control may pass to end.

Figure 8:
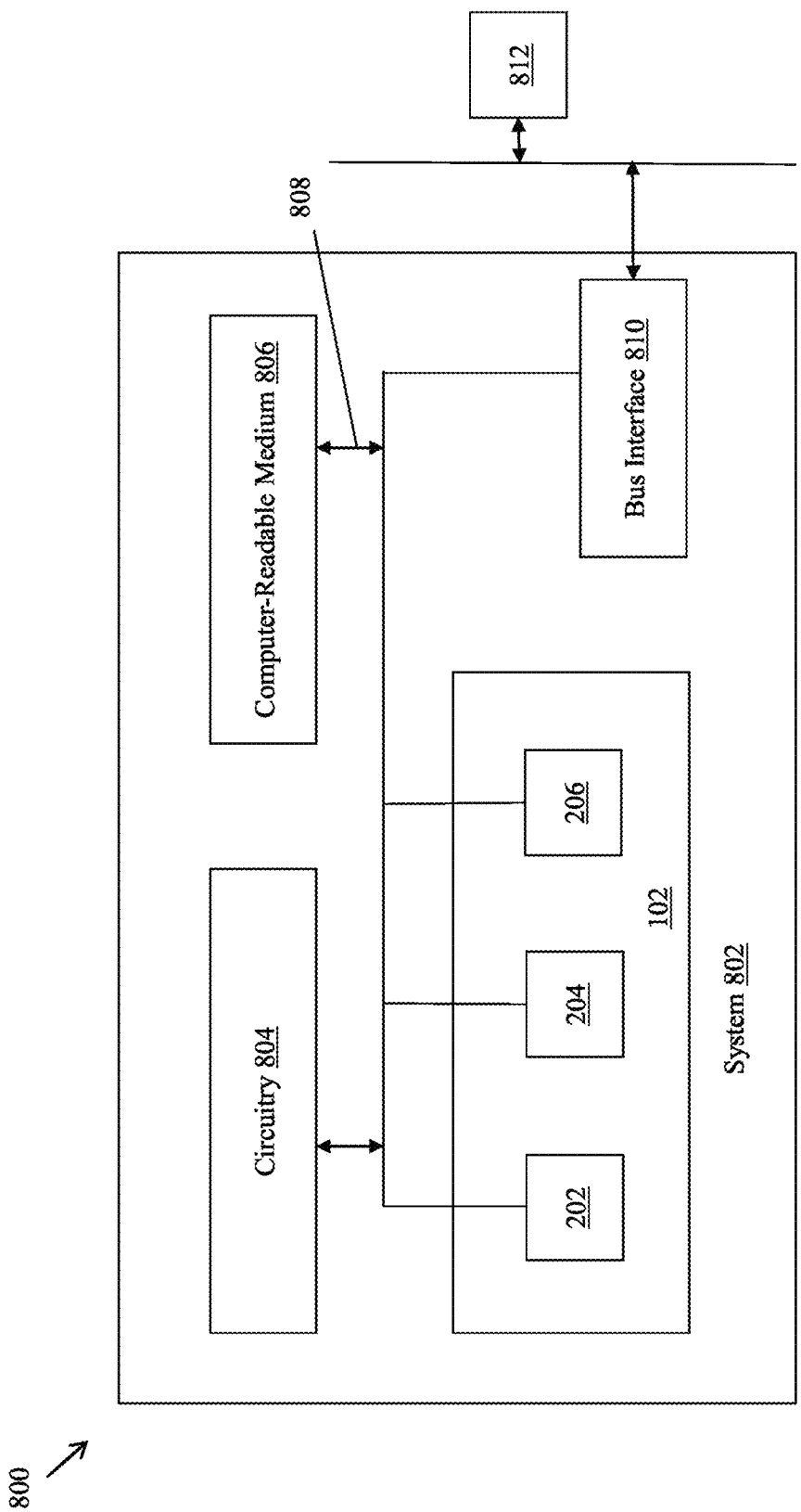
FIG. 8 is a conceptual diagram illustrating an example of a hardware implementation for a system used for medical data governance using large language models, in accordance with an exemplary embodiment of the disclosure.

FIG. 8 is a conceptual diagram illustrating an example of a hardware implementation for a system used for medical data governance using large language models, in accordance with an exemplary embodiment of the disclosure. FIG. 8 is explained in conjunction with elements from FIGS. 1, 2, 3, 4, 5, 6, and 7. Referring to FIG. 8, the hardware implementation shown by a representation 800 for the network environment 100 employs a processing system 802 for magnifying an image based on trained neural networks, in accordance with an exemplary embodiment of the disclosure, as described herein.

In some examples, the processing system 802 may comprise a circuitry 804, a non-transitory computer-readable medium 806, a bus 808, a bus interface 810, and a transceiver 812.

The circuitry 804, such as the circuitry 202, may be configured to manage the bus 808 and general processing, including the execution of a set of instructions stored on the non-transitory computer-readable medium 806. The set of instructions, when executed by the circuitry 804, causes the system 102 to execute the various functions described herein for any particular apparatus. The circuitry 804 may be implemented, based on a number of processor technologies known in the art. Examples of the circuitry 804 may be RISC processor, ASIC processor, CISC processor, and/or other processors or control circuits.

The non-transitory computer-readable medium 806 may be used for storing data that is manipulated by the circuitry 804 when executing the set of instructions. The data is stored for short periods or in the presence of power.

The bus 808 may be configured to link together various circuits. In this example, the network environment 100 employing the processing system 802 and the non-transitory computer-readable medium 806 may be implemented with bus architecture, represented generally by bus 808. The bus 808 may include any number of interconnecting buses and bridges depending on the specific implementation of the system 102 and the overall design constraints. The bus interface 810 may be configured to provide an interface between the bus 808 and other circuits, such as the transceiver 812, and external devices, such as the display device 108A, and the server 110.

The transceiver 812 may be configured to provide a communication of the system 102 with various other apparatus, such as the display device 108A, via a network. The transceiver 812 may communicate via wireless communication with networks, such as the Internet, the Intranet and/or a wireless network, such as a cellular telephone network, a wireless local area network (WLAN) and/or a metropolitan area network (MAN). The wireless communication may use any of a plurality of communication standards, protocols and technologies, such as 5th generation mobile network, Global System for Mobile Communications (GSM), Enhanced Data GSM Environment (EDGE), Long Term Evolution (LTE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VOIP), and/or Wi-MAX.

It should be recognized that, in some embodiments of the disclosure, one or more components of FIG. 8 may include software whose corresponding code may be executed by at least one processor, for across multiple processing environments.

In an aspect of the disclosure, the circuitry 804, the non-transitory computer-readable medium 806, or a combination of both may be configured or otherwise specially programmed to execute the operations or functionality of the circuitry 202, the memory 204, the I/O device 206, the network interface 208, and the inference accelerator 210 or various other components described herein, as described with respect to FIGS. 1 to 8.

Various embodiments of the disclosure comprise the system 102 for medical data governance using large language models. The system 102 may comprise, for example, the circuitry 202, the memory 204, the I/O device 206, and the network interface 208, and/or the inference accelerator 210. The circuitry 202 of the system 102 may be configured to receive the user input including at least one search query to retrieve first medical data from one or more MDG databases 104. The circuitry 202 may be further configured to apply the one or more large language models (LLMs) 106 on the received at least one search query. The one or more LLMs 106 may be pre-trained models. The circuitry 202 of the system 102 may be further configured to determine metadata associated with the at least one search query based on the application of the one or more LLMs 106 on the received search query. The circuitry 202 of the system 102 may be further configured to query the first MDG database 104A of the one or more MDG databases 104 based on the determined metadata to retrieve the first medical data and output the retrieved first medical data.

Certain embodiments of the disclosure may be found in a system, a method, and an electronic device for medical data governance using large language models. Various embodiments of the disclosure may provide the system that may include circuitry configured to receive a user input including at least one search query to retrieve first medical data from one or more medical data governance (MDG) databases. The system may further apply one or more large language models (LLMs) on the received at least one search query. The one or more LLMs may be pre-trained models. The system may further determine metadata associated with the at least one search query based on the application of the one or more LLMs on the received search query. The system may further query a first MDG database of the one or more MDG databases based on the determined metadata to retrieve the first medical data. The system may further output the retrieved first medical data.

In accordance with an embodiment, the system may extract, from the first MDG database, raw data associated with the determined metadata based on querying the first MDG database. The system may further generate one or more constructs associated with the one or more LLMs to be applied on the extracted raw data, wherein the one or more constructs are associated with the determined metadata. The system may further retrieve the first medical data based on the application of the generated one or more constructs on the extracted raw data. The system may further output the retrieved first medical data.

In accordance with an embodiment, the one or more medical data governance (MDG) databases comprises of electronic medical records associated with at least one user.

In accordance with an embodiment, the electronic medical records correspond to at least one of: doctor consultation notes, doctor progress notes, nurses notes, a prescription history, problem lists, International Classification of Diseases (ICD) codes, laboratory results, pathology reports, X-radiation (X-RAY) reports, computed tomography (CT) reports, magnetic resonance imaging (MRI) reports, ultrasound reports, cardiac catheter reports, or cardiac stress reports associated with at least one user.

In accordance with an embodiment, the system may acquire numerical data captured by one or more medical devices associated with at least one user. The system may further generate a description associated with the received numerical data. The system may further store the generated description in at least one of the one or more MDG databases.

In accordance with an embodiment, the system may receive real-time medical data associated with at least one user from one or more medical devices associated with the at least one user. The system may further determine at least one upcoming event associated with a medical condition of the at least one user based on the received real-time medical data and the one or more MDG databases. The system may further output the determined at least one upcoming event.

In accordance with an embodiment, the system may determine at least one keyword from the determined metadata. The at least one keyword is associated with the at least one search query. The system may further select the first MDG database of the one or more MDG databases based on the determined at least one keyword. The system may further query the selected first MDG database of the one or more MDG databases.

In accordance with an embodiment, the at least one keyword corresponds to one of a name of a user, a name of a medical facility, a name of a disease, or a name of a medical procedure.

As utilized herein, the term "exemplary" means serving as a non-limiting example, instance, or illustration. As utilized herein, the terms "for example," and "for example" set off lists of one or more non-limiting examples, instances, or illustrations. As utilized herein, circuitry is "operable" to perform a function whenever the circuitry comprises the necessary hardware and/or code (if any is necessary) to perform the function, regardless of whether performance of the function is disabled, or not enabled, by some user-configurable setting.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (for example, application specific integrated circuits (ASICs)), by program instructions being executed by one or more processors, or by a combination of both. Additionally, these sequences of actions described herein can be considered to be embodied entirely within any non-transitory form of computer readable storage medium having stored therein a corresponding set of computer instructions that upon execution would cause an associated processor to perform the functionality described herein. Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Another embodiment of the disclosure may provide a non-transitory machine and/or computer-readable storage and/or media, having stored thereon, a machine code and/or a computer program having at least one code section executable by a machine and/or a computer, thereby causing the machine and/or computer to perform the steps as described herein for generating a novel molecular structure using a protein structure.

The present disclosure may also be embedded in a computer program product, which comprises all the features enabling the implementation of the methods described herein, and which when loaded in a computer system is able to carry out these methods. Computer program in the present context means any expression, in any language, code or notation, either statically or dynamically defined, of a set of instructions intended to cause a system having an information processing capability to perform a particular function either directly or after either or both of the following: a) conversion to another language, code or notation; b) reproduction in a different material form.

Further, those of skill in the art will appreciate that the various illustrative logical blocks, modules, circuits, algorithms, and/or steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the embodiments disclosed herein may be embodied directly in firmware, hardware, in a software module executed by a processor, or in a combination thereof. A software module may reside in RAM memory, flash memory, ROM memory, EPROM memory, EEPROM memory, registers, hard disk, physical and/or virtual disk, a removable disk, a CD-ROM, virtualized system or device such as a virtual server or container, or any other form of storage medium known in the art. An exemplary storage medium is communicatively coupled to the processor (including logic/code executing in the processor) such that the processor can read information from, and write information to, the storage medium. In the alternative, the storage medium may be integral to the processor.

While the present disclosure has been described with reference to certain embodiments, it will be noted understood by, for example, those skilled in the art that various changes and modifications could be made and equivalents may be substituted without departing from the scope of the present disclosure as defined, for example, in the appended claims. In addition, many modifications may be made to adapt a particular situation or material to the teachings of the present disclosure without departing from its scope. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated. Therefore, it is intended that the present disclosure is not limited to the particular embodiment disclosed, but that the present disclosure will include all embodiments falling within the scope of the appended claims.

What is claimed is:

1. A system using large language models to process medical data comprising: circuitry configured to:
   receive a user input including at least one search query to retrieve first medical data stored in one or more medical data governance (MDG) databases;
   receive real-time medical data associated with at least one user from one or more medical devices associated with the at least one user;
   determine metadata associated with the received at least one search query and the received real-time medical data based on an application of one or more large language models (LLMs) on the received search query and the received real-time medical data;

query at least a first MDG database of the one or more MDG databases based on the determined metadata; and output the retrieved first medical data, wherein the first medical data comprises at least one upcoming event associated with a medical condition of the at least one user.

2. The system according to claim 1, wherein the circuitry is further configured to:
extract, from the first MDG database, raw data associated with the determined metadata based on the querying the first MDG database;
generate one or more constructs associated with the one or more LLMs to be applied on the extracted raw data, wherein the one or more constructs are associated with the determined metadata;
retrieve the first medical data based on the application of the generated one or more constructs on the extracted raw data; and
output the retrieved first medical data.

3. The system according to claim 1, wherein the received real-time medical data comprises of numerical data; and wherein the circuitry is further configured to:
acquire the numerical data captured by the one or more medical devices associated with at least one user;
generate a description associated with the received numerical data; and
determine the metadata associated with the received at least one search query and the received real-time medical data based on an application of one or more large language models (LLMs) on the received search query and the generated description.

4. The system according to claim 1, wherein the one or more LLMs are pre-trained models.

5. The system according to claim 4, wherein the circuitry is further configured to:
generate a training sample comprising the at least one search query, the received real-time medical data, and the determined metadata;
re-train the one or more pre-trained LLMs based on the generated training sample.

6. The system according to claim 1, wherein the circuitry is further configured to:
determine at least one keyword from the determined metadata, wherein the at least one keyword is associated with the at least one search query;
select the first MDG database of the one or more MDG databases based on the determined at least one keyword; and
query the selected first MDG database of the one or more MDG databases.

7. The system according to claim 6, wherein the at least one keyword corresponds to one of: a name of a user, a name of a medical facility, a name of a disease, or a name of a medical procedure.

8. A method of using large language models to process medical data comprising:
receiving a user input including at least one search query to retrieve first medical data stored in one or more medical data governance (MDG) databases;
receiving real-time medical data associated with at least one user from one or more medical devices associated with the at least one user;
determining metadata associated with the received at least one search query and the received real-time medical data based on an application of one or more large language models (LLMs) on the received search query and the received real-time medical data;
querying at least a first MDG database of the one or more MDG databases based on the determined metadata; and
outputting the retrieved first medical data, wherein the first medical data comprises at least one upcoming event associated with a medical condition of the at least one user.

9. The method according to claim 8, further comprising:
extracting, from the first MDG database, raw data associated with the determined metadata based on the querying the first MDG database;
generating one or more constructs associated with the one or more LLMs to be applied on the extracted raw data, wherein the one or more constructs are associated with the determined metadata;
retrieving the first medical data based on the application of the generated one or more constructs on the extracted raw data; and
outputting the retrieved first medical data.

10. The method according to claim 8, wherein the received real-time medical data comprises of numerical data; and the method further comprising:
acquiring the numerical data captured by the one or more medical devices associated with at least one user;
generating a description associated with the received numerical data; and
determining the metadata associated with the received at least one search query and the received real-time medical data based on an application of one or more large language models (LLMs) on the received search query and the generated description.

11. The method according to claim 8, wherein the one or more LLMs are pre-trained models.

12. The method according to claim 11, further comprising:
generating a training sample comprising the at least one search query, the received real-time medical data, and the determined metadata;
re-training the one or more pre-trained LLMs based on the generated training sample.

13. The method according to claim 8, further comprising:
determining at least one keyword from the determined metadata, wherein the at least one keyword is associated with the at least one search query;
selecting the first MDG database of the one or more MDG databases based on the determined at least one keyword; and
querying the selected first MDG database of the one or more MDG databases.

14. The method according to claim 13, wherein the at least one keyword corresponds to one of: a name of a user, a name of a medical facility, a name of a disease, or a name of a medical procedure.

15. A non-transitory computer-readable medium including computer program instructions, which when executed by a system, cause the system to perform one or more operations comprising:
receiving a user input including at least one search query to retrieve first medical data stored in one or more medical data governance (MDG) databases;
receiving real-time medical data associated with at least one user from one or more medical devices associated with the at least one user;
determining metadata associated with the received at least one search query and the received real-time medical data based on an application of one or more large language models (LLMs) on the received search query and the received real-time medical data;

querying at least a first MDG database of the one or more MDG databases based on the determined metadata; and outputting the retrieved first medical data, wherein the first medical data comprises at least one upcoming event associated with a medical condition of the at least one user.

16. The non-transitory computer-readable medium according to claim 15, further comprising: extracting, from the first MDG database, raw data associated with the determined
  metadata based on the querying the first MDG database;
    generating one or more constructs associated with the one or more LLMs to be applied on the extracted raw data, wherein the one or more constructs are associated with the determined metadata;
    retrieving the first medical data based on the application of the generated one or more constructs on the extracted raw data; and
    outputting the retrieved first medical data.

17. The non-transitory computer-readable medium according to claim 15, further comprising: acquiring numerical data captured by the one or more medical devices associated
  with at least one user, wherein the received real-time medical data comprises of the numerical data;
    generating a description associated with the received numerical data; and
    determining the metadata associated with the received at least one search query and the received real-time medical data based on an application of one or more large language models (LLMs) on the received search query and the generated description.

18. The non-transitory computer-readable medium according to claim 15, further comprising:
  generating a training sample comprising the at least one search query, the received real-time medical data, and the determined metadata;
  training the one or more LLMs based on the generated training sample.

19. The non-transitory computer-readable medium according to claim 15, further comprising: determining at least one keyword from the determined metadata, wherein the at
  least one keyword is associated with the at least one search query;
    selecting the first MDG database of the one or more MDG databases based on the determined at least one keyword; and
    querying the selected first MDG database of the one or more MDG databases.

20. The non-transitory computer-readable medium according to claim 19, wherein the at least one keyword corresponds to one of: a name of a user, a name of a medical facility, a name of a disease, or a name of a medical procedure.

* * * * *